US008131469B2

(12) United States Patent  (10) Patent No.: US 8,131,469 B2
Chen et al.  (45) Date of Patent: Mar. 6, 2012

(54) DATA ACQUISITION AND PROCESSING FOR INVASION PROFILE AND GAS ZONE ANALYSIS WITH NMR DUAL OR MULTIPLE INTERECHO SPACING TIME LOGS

(75) Inventors: Songhua Chen, Katy, TX (US); Wei Shao, Conroe, TX (US)

(73) Assignee: Baker Hughes Incorporated, Houston, TX (US)

( * ) Notice: Subject to any disclaimer, the term of this patent is extended or adjusted under 35 U.S.C. 154(b) by 765 days.

(21) Appl. No.: 12/245,121

(22) Filed: Oct. 3, 2008

(65) Prior Publication Data

US 2010/0088033 A1 Apr. 8, 2010

(51) Int. Cl.
G01V 1/40 (2006.01)
(52) U.S. Cl. .......................................................... 702/8
(58) Field of Classification Search ...................... 702/8
See application file for complete search history.

(56) References Cited

U.S. PATENT DOCUMENTS

| | | | |
|---|---|---|---|
| 5,498,960 A | 3/1996 | Vinegar et al. | |
| 6,005,389 A | 12/1999 | Prammer | |
| 6,032,101 A | 2/2000 | Freedman et al. | |
| 6,331,775 B1 | 12/2001 | Thern et al. | |
| 6,377,042 B1 | 4/2002 | Menger et al. | |
| 6,937,014 B2 | 8/2005 | Sun et al. | |
| 6,972,564 B2 | 12/2005 | Chen et al. | |
| 7,253,617 B1 | 8/2007 | Chen et al. | |
| 2004/0008027 A1* | 1/2004 | Prammer ..................... 324/303 |
| 2004/0104048 A1 | 6/2004 | Woodburn et al. | |
| 2004/0222791 A1 | 11/2004 | Chen | |
| 2006/0290350 A1 | 12/2006 | Hursan et al. | |
| 2008/0234937 A1 | 9/2008 | Fang et al. | |

OTHER PUBLICATIONS

Fang, et al. "Quantification of Hydrocarbon Saturation in Carbonate Formations Using Simultaneous Inversion of Multiple NMR Echo Trains". SPE 90569. SPE Annual Technical Conference and Exhibition held in Houston, Texas, USA Sep. 26-29, 2004.
International Search Report and Written Opinion, Mailed May 18, 2010, International Appln. No. PCT/US2009/059160, Written Opinion 5 pages, International Search Report 7 pages.

* cited by examiner

Primary Examiner — Aditya Bhat
(74) Attorney, Agent, or Firm — Cantor Colburn LLP

(57) ABSTRACT

A method for obtaining a parameter of interest related to an earth formation, the method including: obtaining nuclear magnetic resonance (NMR) data from an NMR tool investigating the earth formation with a plurality of pulse sequences of radio frequency energy, each pulse sequence having a unique frequency, a first train of pulses having a first interecho time ($TE_1$) and a second train of pulses having a second interecho time ($TE_2$) different from the first interecho time; relating the NMR data to a partial porosity at points to establish an NMR response model; solving the NMR response model to calculate the partial porosity at each of the points in the earth formation; summing the partial porosity for each of the points corresponding to each depth of investigation to provide a pore volume; and associating each pore volume with the corresponding depth of investigation to provide the parameter of interest.

22 Claims, 9 Drawing Sheets

DATA ACQUISITION AND PROCESSING FOR INVASION PROFILE AND GAS ZONE ANALYSIS WITH NMR DUAL OR MULTIPLE INTERECHO SPACING TIME LOGS

BACKGROUND OF THE INVENTION

1. Field of the Invention

The present disclosure relates generally to a downhole nuclear magnetic resonance (NMR) apparatus, data processing, and interpretation methods for evaluating a characteristic of a region, and particularly for detecting and quantifying a light hydrocarbon-bearing earth formation in a subterranean region.

2. Description of the Related Art

Exploration and production of hydrocarbons generally requires that a borehole be drilled into an earth formation. The borehole provides access to the earth formation for performing measurements related to a property of the formation. Many wireline and logging-while-drilling (LWD) tools probe the formation in the shallow region of radial depths surrounding the borehole. The information gathered by these tools in the shallow radial depths of investigation often are contaminated by invasion of drilling fluid, also known as mud filtrate invasion. In order to accurately quantify hydrocarbon saturation and predict multiphase flow in the earth formation, petrophysicists are interested in determining the hydrocarbon and invading filtrate fluid volumes and saturations as a function of radial depth. The variation of mud filtrate saturation is often more pronounced in gas reservoirs due to the high mobility of gas. It is suspected that mud filtrate invasion may vary within a few inches in the flushed zone.

In the prior art, three approaches have generally been used to detect invasion variations and generate an invasion profile. The invasion profile is a correlation of depth to an amount of invasion. The first approach compares density porosity with NMR apparent porosity corresponding to depth of invasion (and, thus frequency). The first approach requires knowledge of the matrix density and, therefore, is subject to the accuracy of the technique for determining the matrix density. Furthermore, since density porosity does not have a well defined depth of invasion, the variation of NMR apparent porosity only reflects the relative variation of flushed zone gas saturation, not the absolute gas zone saturation. The second approach applies a linear constraint to simultaneous inversion of all frequency data obtained from NMR measurements. The second approach works only if the invasion variation is consistent to the constraint but will be less effective for the case where gas replenishes the flushed zone long after the mud cake builds up. An independently measured gas saturation profile is desired. The third approach acquires NMR T2 distribution logs corresponding to a plurality of depths of investigation and observes the differences between the logs.

Three approaches using NMR are also generally used for the detection of gas. The first approach is based on T1 contrast between a slowly relaxing gas and a fast relaxing liquid. The first approach is less effective for gas zones having water in very large pores and/or containing light oil or oil-based-mud-filtrate (OBMF). The second approach is based on $T_1/T_{2app}$ contrast where apparent $T_2$ relaxation time, $T_{2app}$, is reduced from intrinsic $T_2$ relaxation time, $T_{2intr}$, due to diffusion effect, which causes additional diffusion-induced decay in a magnetic gradient environment. Since the diffusivity of gas is much higher than that of liquid phase hydrocarbon and water, the ratio for gas is much larger than that for the liquids. The third approach is based on a hydrogen index effect.

The gas detection methods based on $T_1$ or $T_1/T_{2app}$ usually require a long data acquisition time for measuring NMR signal build-up at multiple stages of polarization. Compared to CPMG $T_2$ measurement, $T_1$ is an inefficient method in terms of the amount of data in a unit of time. Thus, usually the logging speed has to be reduced for the $T_1$ log. As a result, $T_1$ logging is more useful in LWD than in wireline logging. In order to increase the logging speed, a multi-frequency NMR tool is used such that within the time waiting for the NMR tool to polarize protons in the zone of investigation back to the full-polarization state, the NMR tool can acquire data at different frequencies, corresponding to different depths of investigation. By distributing different wait times among these frequencies, one can successfully acquire multiple stages of polarization among the different frequencies and then process the data together as if the data were obtained from the same polarization build-up. This last process excludes significant variations in formation properties or in an invasion zone. For a relatively narrow range of depths of invasion and for low-mobility fluids, the variation of invasion may be insignificant. Occasionally, the high mobility gas may cause slight variation of invasion within a few inches.

Unlike $T_2$ measurements, $T_1$ logging data provides the intrinsic relaxation time because diffusion induced decay, $$\frac{1}{T_{2diff}} = \frac{(\gamma \cdot G \cdot TE)^2 \cdot D}{12}, \tag{1}$$

affects only $T_1$ measurements. To reduce the diffusion effect on $T_2$ measurements, one must reduce $G \cdot TE$, which is subjected to limitations of the NMR tool.

Therefore, what are needed are techniques for acquiring NMR data efficiently and yet providing a relaxation time substantially close to the intrinsic relaxation time.

BRIEF SUMMARY OF THE INVENTION

Disclosed is a method for obtaining a parameter of interest related to an earth formation, the method including: obtaining nuclear magnetic resonance (NMR) data from an NMR tool investigating the earth formation with a plurality of pulse sequences of radio frequency energy, each pulse sequence having a unique frequency, a first train of pulses having a first interecho time ($TE_1$) and a second train of pulses having a second interecho time ($TE_2$) different from the first interecho time; relating the NMR data to a partial porosity at points (i,j) related to a first apparent transverse relaxation time ($T_{2,app,TE1,i}$) obtained with ($TE_1$) and a second apparent transverse relaxation time ($T_{2,app,TE2,j}$) obtained with ($TE_2$) to establish an NMR response model; solving the NMR response model to calculate at least one of the partial porosity and a fluid-filled pore volume at each of the points in the earth formation; summing at least one of the partial porosity and the fluid-filled pore volume for each of the points corresponding to each depth of investigation to provide at least one of a pore volume and a total fluid-filled pore volume; and associating at least one of each pore volume and each total fluid-filled pore volume with the corresponding depth of investigation to provide the parameter of interest.

Also disclosed is an apparatus for obtaining a parameter of interest related to an earth formation, the apparatus including: a processing system configured to implement the following instructions: obtaining nuclear magnetic resonance (NMR) data from an NMR tool investigating the earth formation with a plurality of pulse sequences of electromagnetic energy, each pulse sequence having a unique frequency, and a first train of pulses with a first interecho time ($TE_1$) and a second train of pulses having a second interecho time ($TE_2$) different from the first interecho time, the tool establishing a magnetic field gradient in the earth formation wherein a depth of investigation corresponds with each frequency and the magnetic field gradient; relating the NMR data to a partial porosity at points (i,j) related to a first apparent transverse relaxation time ($T_{2,app,TE1,i}$) obtained with ($TE_1$) and a second apparent transverse relaxation time ($T_{2,app,TE2,j}$) obtained with ($TE_2$) to establish an NMR response model; solving the NMR response model to calculate at least one of the partial porosity and a fluid-filled pore volume at each of the points in the earth formation; summing at least one of the partial porosity and the fluid-filled pore volume for each of the points corresponding to each depth of investigation to provide at least one of a pore volume and a total fluid-filled pore volume; and associating at least one of each pore volume and each total fluid-filled pore volume with the corresponding depth of investigation to provide the parameter of interest.

Further disclosed is a computer program product stored on machine-readable media having machine-executable instructions for obtaining a parameter of interest related to an earth formation, by implementing a method including: obtaining nuclear magnetic resonance (NMR) data from an NMR tool investigating the earth formation with a plurality of pulse sequences of electromagnetic energy, each pulse sequence having a unique frequency, and a first train of pulses with a first interecho time ($TE_1$) and a second train of pulses having a second interecho time ($TE_2$) different from the first interecho time, the tool establishing a magnetic field gradient in the earth formation wherein a depth of investigation corresponds with each frequency and the magnetic field gradient; relating the NMR data to a partial porosity at points (i,j) related to a first apparent transverse relaxation time ($T_{2,app,TE1,i}$) obtained with ($TE_1$) and a second apparent transverse relaxation time ($T_{2,app,TE2,j}$) obtained with ($TE_2$) to establish an NMR response model; solving the NMR response model to calculate at least one of the partial porosity and a fluid-filled pore volume at each of the points in the earth formation; summing at least one of the partial porosity and the fluid-filled pore volume for each of the points corresponding to each depth of investigation to provide at least one of a pore volume and a total fluid-filled pore volume; and associating at least one of each pore volume and each total fluid-filled pore volume with the corresponding depth of investigation to provide the parameter of interest.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like numbered elements are numbered alike, in which:

DETAILED DESCRIPTION OF THE INVENTION

Figure 1:
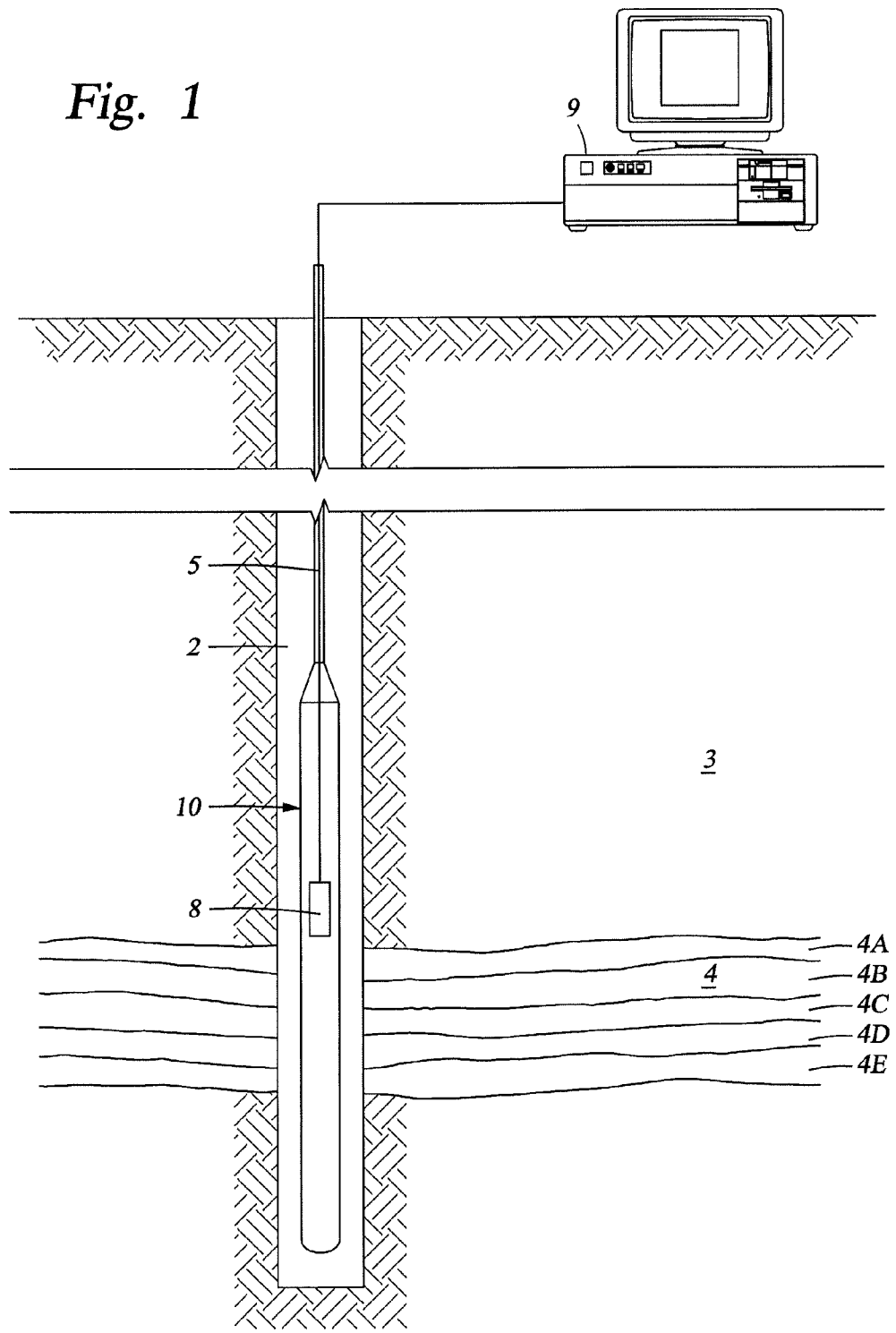
FIG. 1 illustrates an exemplary embodiment of a logging tool disposed in a borehole penetrating the earth.

Disclosed are embodiments of techniques for acquiring data efficiently from a nuclear magnetic resonance (NMR) instrument while providing a relaxation time substantially close the intrinsic relaxation time. The techniques, which include apparatus and method, call for obtaining NMR data from a formation being investigated using at least two different interecho times (TE). The first TE is small, such as 3 milliseconds (ms). The corresponding distribution of transverse relaxation times $T_2$ is substantially close to intrinsic relaxation time for fluids having slow diffusion. The second TE is considerably larger than the first TE. The value of the second TE may vary for different fluids and different NMR tools. The MREX$^{SM}$ tool, available from Baker Hughes Corporation of Houston, Tex., is one example of an NMR tool that can be used to acquire NMR using the techniques disclosed herein. For gas detection using the MREX tool, the second TE can be selected to be 1.0 ms. This number (1.0 ms) of course can be changed if necessary depending on the tool and the medium to be detected. The two TEs can be extended to more than two, and the dual or multiple TE acquisition elements can be integrated to the objective-oriented logging sequence described in U.S. Pat. No. 6,972,564 by Chen and Edwards.

Although in general it is not required to choose the same TE pairs for different frequency in a multifrequency data acquisition scheme, for invasion profile detection, the same TE pairs repeated for all frequencies makes it easier to compare the results acquired from different frequencies.

The NMR tool can perform NMR measurements at various distances into the formation based upon an intensity of a magnetic field gradient applied to the formation and a frequency used for sequences of pulses of electromagnetic energy referred to in the art as Carr-Purcell-Meiboom-Gill spin echo measurement sequences (i.e., CPMG sequences). The pulses of electromagnetic energy are generally in the radio frequency range. The distance used for an NMR measurement is referred to as "depth of investigation." The depth of investigation is generally measured from a borehole, into which the NMR tool is disposed, to a distance into the formation.

A response model can be established relating the NMR data, which is a response from the NMR tool, to various NMR data acquisition parameters, such as the two different interecho times, and a property of the earth formation, such as porosity. Inversion is then performed on the response model to determine the porosity at points in the earth formation. By summing the porosity at the points associated with a specific depth of investigation, a total pore volume can be calculated for the specific depth of investigation. Furthermore, the total pore volume can be subdivided into gas-bearing pore volume and liquid-bearing (i.e., filtrate, water, etc.) pore volumes as determined from the NMR measurements. Each filtrate pore volume can be plotted against an associated depth of investigation to produce a filtrate invasion profile. On the other hand, changes in pore volume along the borehole depths can be used as an indication of a boundary between layers in the formation.

For convenience, certain definitions are presented. The term "interecho time" relates to the time between two adjacent echoes. The term "wait time" (TW) relates to the time allotted for the alignment of protons with the applied magnetic field strength during an NMR measurement. The term "longitudinal relaxation time" ($T_1$) relates to a time constant describing hydrogen atoms during an NMR measurement as they lose energy and align with an applied magnetic field gradient. The term "transverse relaxation time" ($T_2$) relates to a time constant describing protons losing coherent energy during an NMR measurement. "$T_{2app}$" represents apparent transverse relaxation time. "$T_{2,diff}$" represents transverse relaxation time due to diffusion-induced decay under a magnetic field gradient. "$T_{2,int}$" represents intrinsic transverse relaxation time. "R" represents the ratio $T_1/T_{2,int}$.

Referring to FIG. 1, a well logging tool 10 is shown disposed in a borehole 2. The borehole 2 is drilled through earth 3 and penetrates a formation 4, which include various formation layers 4A-4E (and boundaries between the layers). In the embodiment of FIG. 1, the logging instrument 10 is lowered into and withdrawn from the borehole 2 by use of an armored electrical cable 5 or similar conveyance as is known in the art. In other embodiments, the logging tool 10 may perform measurements, referred to as logging-while-drilling (LWD), during drilling operations or during a temporary halt.

The logging tool 10 as shown in FIG. 1 is configured to perform NMR measurements on the formation 4. In order to perform the NMR measurements and collect NMR data, the logging instrument 10 includes NMR components as known in the art. Non-limiting examples of the NMR components include an antenna, a transmitter, a receiver, and a magnet. In the embodiment of FIG. 1, the logging tool 10 includes an electronic unit 8. The electronic unit 8 can be configured to transmit the NMR data from the logging tool 10 to a processing system 9 at the surface of the earth 3 using the electrical cable 5 or a telemetry system for LWD applications. In addition, for LWD applications, the NMR data can be stored in the electronic unit 8 for later retrieval when the logging instrument 10 is removed from the borehole 2.

In general, the borehole 2 includes materials such as would be found in oil exploration, including a mixture of liquids such as water, drilling fluid, mud, oil, gas and formation fluids that are indigenous to the various formations.

In a preferred implementation, the data acquisition sequence includes trainlets at 0.3 ms, and the long echo trains are TE=0.3 ms and 1.0 ms, respectively, with 800 ms echo length. (In other embodiments, other interecho times and echo lengths can be used.) The same combination is repeated for every frequency. Trainlets with these parameters are generally used to detect clay-bound-water (CBW).

A variation of the data acquisition method includes using two frequencies to obtain multiple TW data and the remaining frequencies acquire dual TE data as described above. Thus we should have both the $T_1/T_{2app}$ ratio and $T_{2,app}(0.3)/T_{2,app}(1.0)$ ratio.

Interpreting features of gas from data obtained using the two different TEs is discussed next. In a substantially large magnetic field gradient, such as that of the MREX tool, the apparent $T_2$ is dominated by diffusion-induced decay, thus if we choose TE=0.3 ms and 1.0 ms, respectively, the ratio of $T_{2,app}$ is approximately $$\frac{T_{2,app}(TE_2 = 0.3 \text{ ms})}{T_{2,app}(TE_1 = 1.0 \text{ ms})} \approx \frac{T_{2,diff}(TE_2 = 0.3 \text{ ms})}{T_{2,diff}(TE_1 = 1.0 \text{ ms})} = \left(\frac{1.0}{0.3}\right)^2 \approx 11 \quad (2)$$

Figure 2:
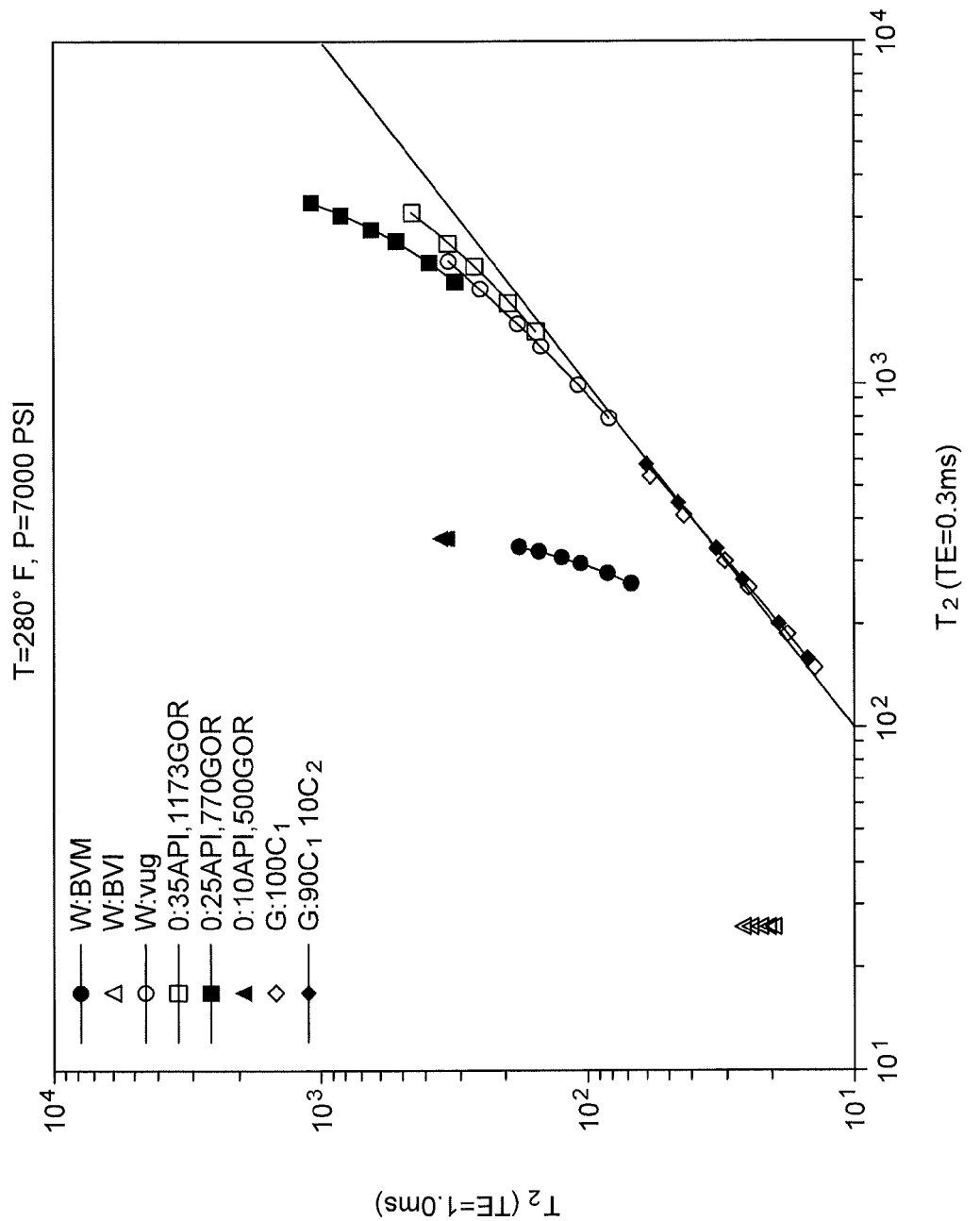
FIG. 2 illustrates an example of a plot of transverse relaxation time $T_2$ for a first interecho time versus $T_2$ for a second interecho time for a first set of parameters.
Figure 3:
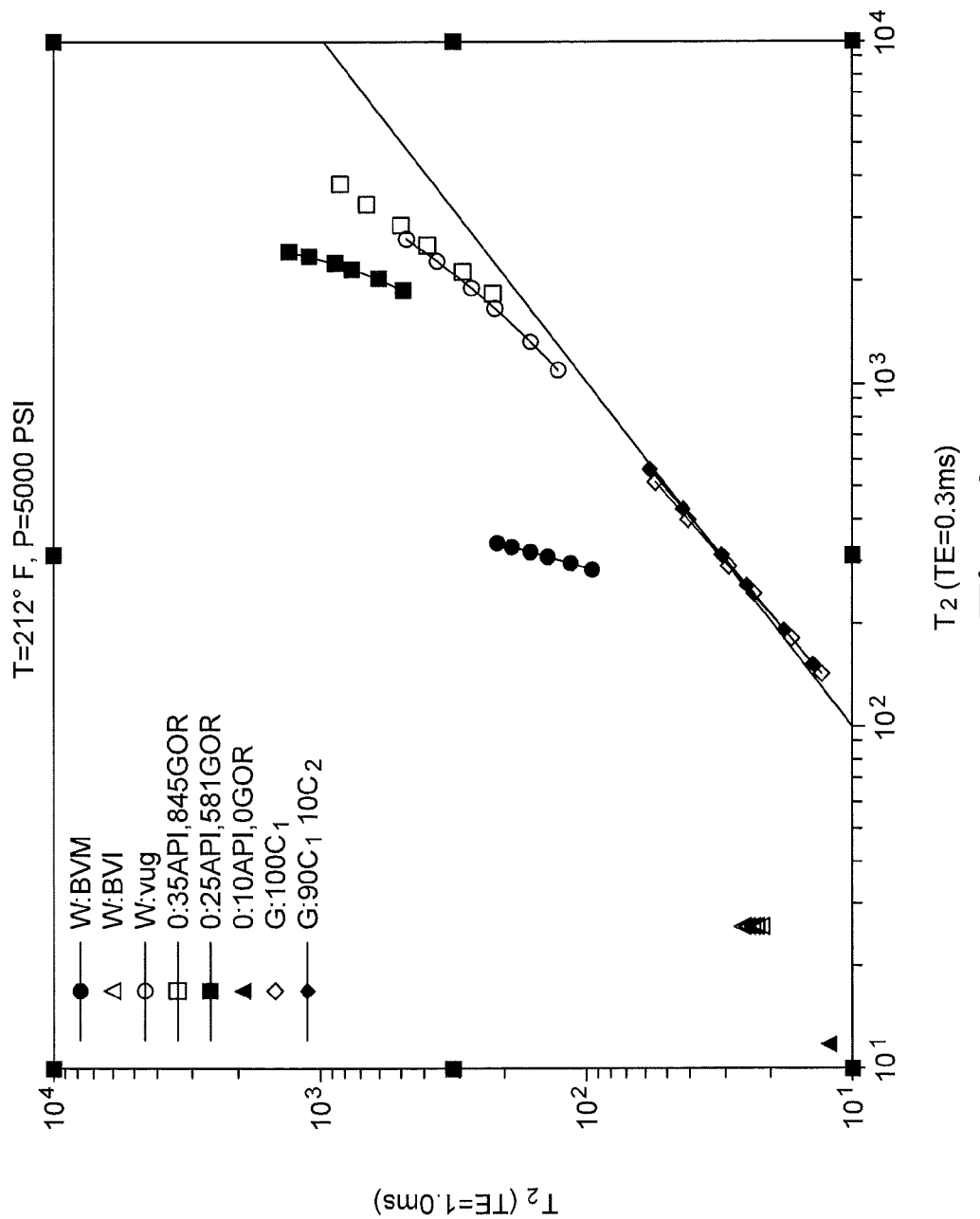
FIG. 3 illustrates another example of a plot of $T_2$ for a first interecho time versus $T_2$ for a second interecho time for a second set of parameters.
Figure 4:
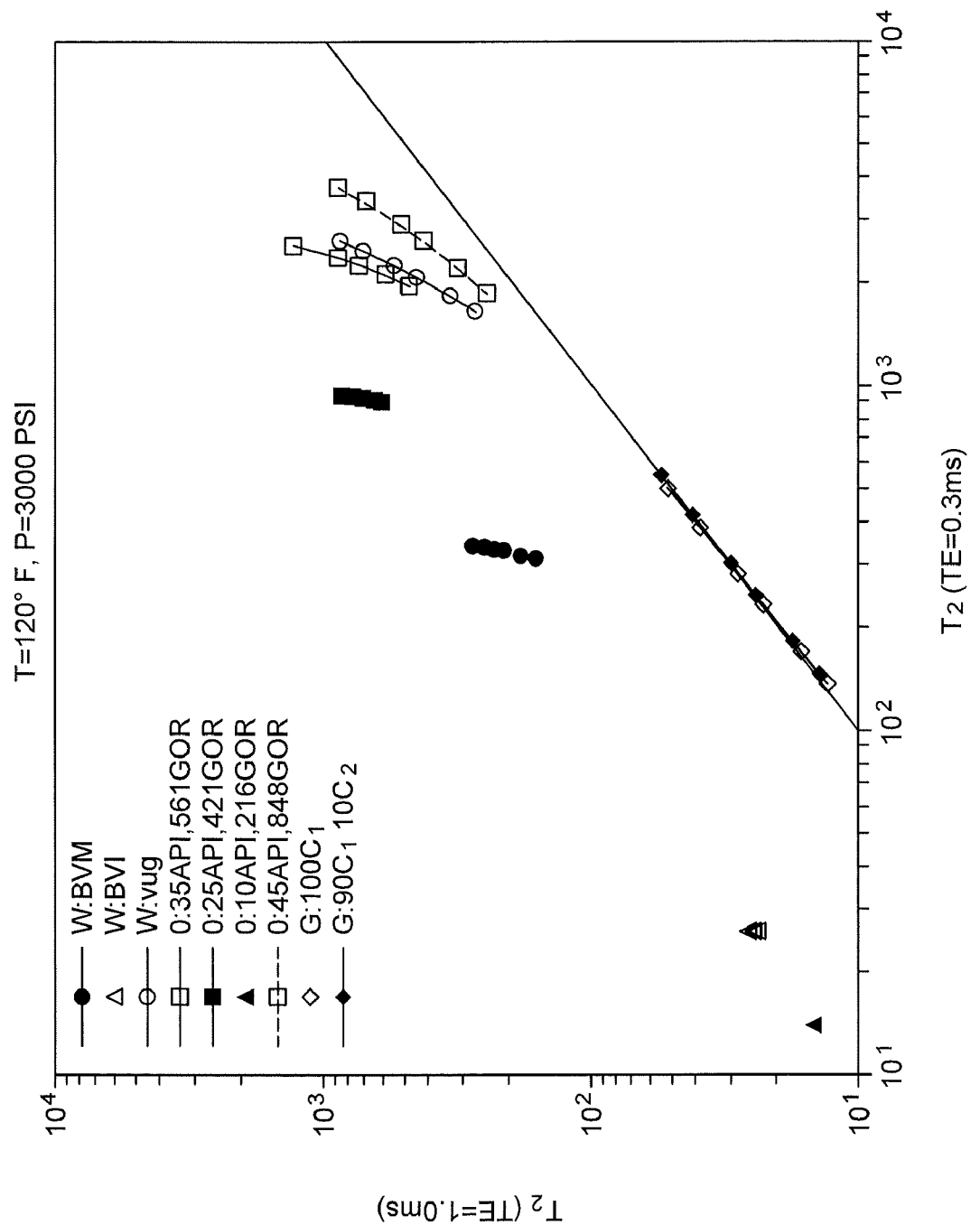
FIG. 4 illustrates another example of a plot of $T_2$ for a first interecho time versus $T_2$ for a second interecho time for a third set of parameters.
Figure 5:
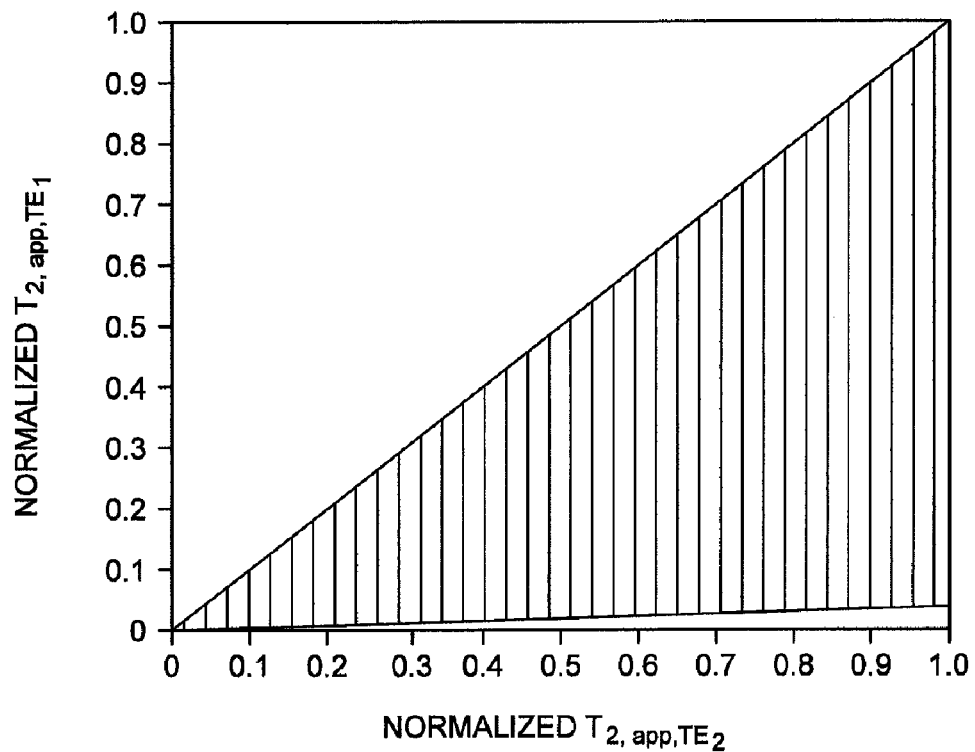
FIG. 5 illustrates a graph of solution constraints in solving for $T_2$ apparent for the first interecho time and $T_2$ apparent for the second interecho time.
Figure 6:
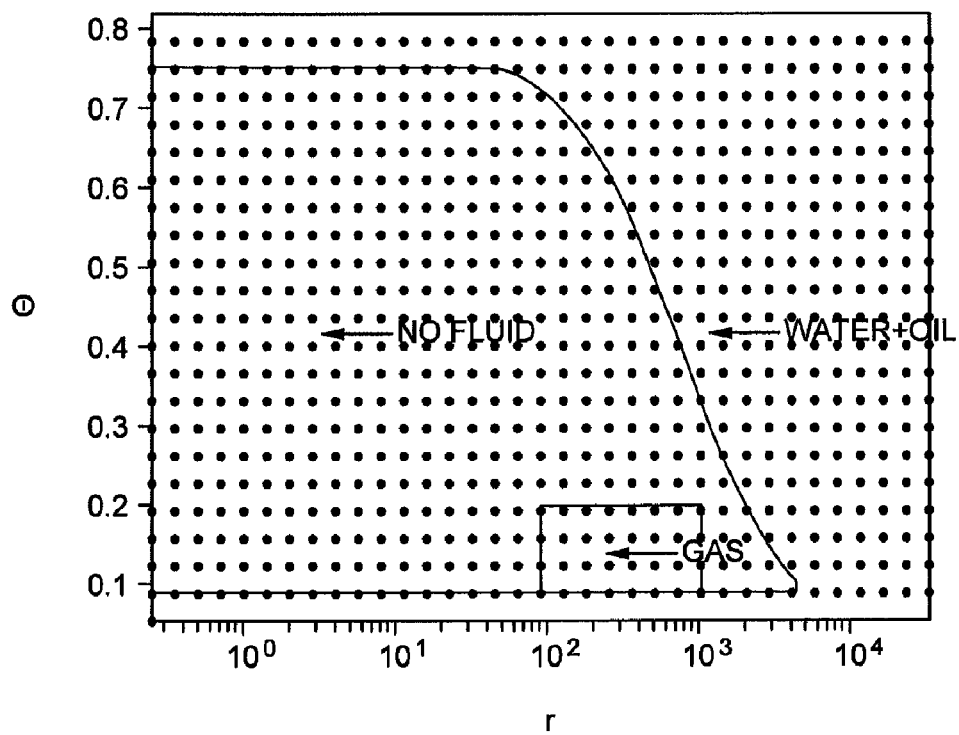
FIG. 6 illustrates an exemplary embodiment of parameter space for distribution patterns of gas and liquid in an r-θ plane.

Since the gas $T_{2,app}$ is dominated by the diffusion induced decay, this ratio is not dependent on temperature or pressure, and is also independent of internal gradient. Furthermore, it works for a mixture of hydrocarbon gases. For instance, because both methane and ethane have large diffusion coefficients, mixtures including methane or ethane are also dominated by diffusion decay. This feature is illustrated in FIGS. 2-4, where the apparent $T_2$ values for both 100% $CH_4$ and 90% $CH_4$+10% $C_2H_6$ gases are shown in these plots.

The $T_{2,app}$(TE=0.3ms) value of gas is dependent on the magnetic gradient and the frequency range of the MREX instrument, the value is generally in the range of about 100-600 ms. A line is drawn intercepting at coordinates (100, 10) and (10000, 1000). It can be seen that gas symbols are all on a segment of that line where no oil and water is close to that segment.

Compared to the $T_1/T_{2,app}$ ratio method, which is dependent on frequency and internal-gradient, interpretation is simpler with $$\frac{T_{2,app}(TE_2 = 0.3 \text{ ms})}{T_{2,app}(TE_1 = 1.0 \text{ ms})}$$

and in general, as long as TE is not so small such that gas $T_{2,app}$ is no longer dominated by $T_{2,diff}$, we can generalize to other TE values and the ratio is $$\frac{T_{2,app,TE_1}}{T_{2,app,TE_2}} \approx \frac{T_{2,diff,TE_1}}{T_{2,diff,TE_2}} = \left(\frac{TE_2}{TE_1}\right)^2. \quad (3)$$

Because the ratio described in equation (2) is frequency independent, we can stack (i.e., group data prior to inversion processing) all frequency data together to improve signal-to-noise ratio and further reduce the vertical stacking, if the invasion profile is determined not to be not important in a formation of interest.

In another embodiment, data acquired with individual frequencies are processed separately to determine the apparent porosity and the gas saturation. These results are further plotted in terms of depth of invasion (DOI) to view the invasion profile.

In yet another embodiment, the different frequency data are plotted on the same figure (See FIGS. 1-3 and the corresponding captions for the explanation) without stacking, it may be helpful to identify gas by observing that the gas porosities are on the (100,0) to (0,1000) line.

Aspects of a method for processing data are presented next in three parts—Part (a), Part (b) and Part (c).

Part (a)—Description of Dual Apparent $T_2$ Model:

One embodiment of the data processing methods is to use an echo decay model, which includes both the intrinsic $T_2$ and diffusivity D. The effect of diffusivity in a gradient magnetic field adds an additional decay term to the intrinsic transverse relaxation decay, resulting in the measured apparent transverse relaxation time, $T_{2,app}$ as shown in the following equation:

$$\frac{1}{T_{2,app}} = \frac{1}{T_{2,int}} + \frac{D(\gamma G \cdot TE)^2}{12}. \qquad (4)$$

For data acquired with two different TEs:

$$\frac{1}{T_{2,app,TE_1}} = \frac{1}{T_{2,int}} + \frac{D(\gamma G_1 \cdot TE_1)^2}{12} \text{ and} \qquad (5)$$

$$\frac{1}{T_{2,app,TE_2}} = \frac{1}{T_{2,int}} + \frac{D(\gamma G_2 \cdot TE_2)^2}{12} \qquad (6)$$

where $T_{2,app,TE_1}$ is the apparent $T_2$ with $TE_1$ and gradient of $G_1$, and $T_{2,app,TE_2}$ is the apparent $T_2$ with $TE_2$ and gradient of $G_2$, and $\gamma$ is the gyromagnetic ratio.

From equations (5) and (6), the fluid properties D and $T_{2,int}$ can be expressed in terms of the measured apparent $T_{2,app}$ of dual TE acquisition data, the tool 10 acquisition parameter G, the data acquisition parameter TE, and the diffusivity by:

$$D = \frac{12}{(\gamma G_1 \cdot TE_1)^2 - (\gamma G_2 \cdot TE_2)^2} \left( \frac{1}{T_{2,app,TE_1}} - \frac{1}{T_{2,app,TE_2}} \right), \qquad (7)$$

and the intrinsic relaxation term by:

$$\frac{1}{T_{2,int}} = (1-\lambda)\frac{1}{T_{2,app,TE_1}} + \lambda \frac{1}{T_{2,app,TE_2}}, \qquad (8)$$

where $$\lambda = \frac{(G_1 \cdot TE_1)^2}{(G_1 \cdot TE_1)^2 - (G_2 \cdot TE_2)^2} \qquad (9)$$

depends only on the tool 10 and data acquisition parameters.

Using the above description, we express the NMR response in terms of the apparent $T_{2,app,TE_1}$, the apparent $T_{2,app,TE_2}$, and a partial porosity $p_{i,j}$ that corresponds to the i-th $T_{2,app,TE_1,i}$ and the j-th $T_{2,app,TE_2,j}$ (i.e., points in the $T_{2,app,TE_1}$ and $T_{2,app,TE_2}$ parameter space):

$$M(t, TW, TE, G, R) = \qquad (10)$$

$$\sum_i \sum_j p_{i,j} \left\{ 1 - \exp\left[ -\frac{TW}{R}\left[ (1-\lambda)\frac{1}{T_{2,app,TE_1,i}} + \lambda \frac{1}{T_{2,app,TE_2,j}} \right] \right] \right\} \times$$

$$\exp\left[ -(1-\lambda)\frac{t}{T_{2,app,TE_1,i}} - \lambda \frac{t}{T_{2,app,TE_2,j}} \right] \times \exp$$

$$\left\{ -\frac{(G_1 \cdot TE_1)^2 \cdot t}{(G_1 \cdot TE_1)^2 - (G_2 \cdot TE_2)^2} \left( \frac{1}{T_{2,app,TE_1,i}} - \frac{1}{T_{2,app,TE_2,j}} \right) \right\}$$

where $G_1 \cdot TE_1 > G_2 \cdot TE_2$ is assumed, thus $$\frac{T_{2,app,TE_1}}{T_{2,app,TE_2}} < 1. \qquad (11)$$

Applying the non-negativity constraint for the relaxation rate $$\frac{1}{T_{2,int}} > 0,$$

we have $$\frac{T_{2,app,TE_1}}{T_{2,app,TE_2}} > \frac{\lambda - 1}{\lambda} = \frac{(G_2 \cdot TE_2)^2}{(G_1 \cdot TE_1)^2}. \qquad (12)$$

Combining equations (11) and (12), the following is obtained:

$$1 > \frac{T_{2,app,TE_1}}{T_{2,app,TE_2}} > \frac{(G_2 \cdot TE_2)^2}{(G_1 \cdot TE_1)^2}. \qquad (13)$$

Part (b)—Parameter Space Transformation:

The inequality presented in equation (13) indicates that the NMR responses are confined to a triangle-shaped area defined by $$\frac{(G_2 \cdot TE_2)^2}{(G_1 \cdot TE_1)^2}$$

and 1, in the $T_{2,app,TE_1}$ and $T_{2,app,TE_2}$ parameter space, as illustrated in FIG. 4. The hatched area is more conveniently described in the polar coordinate system, which makes it simpler to set the inversion parameters. For this purpose, the $T_{2,app,TE_1}$ and $T_{2,app,TE_2}$ parameter space is converted into the (r, θ) polar coordinate system as follows:

$$r = \sqrt{T_{2,app,TE_1}^2 + T_{2,app,TE_2}^2}$$

$$\theta = \tan^{-1}\frac{T_{2,app,TE_1}}{T_{2,app,TE_2}},$$

$$\text{and } \frac{\pi}{4} > \theta > \tan^{-1}\left( \frac{(G_2 * TE_2)^2}{(G_1 * TE_1)^2} \right).$$

In the polar coordinate system, the echo train decay can be described in terms of (r, θ):

$$M(t, TW, TE, G, R) = \qquad (14)$$

$$\sum_i \sum_j p_{i,j} \left\{ 1 - \exp\left[ -\frac{TW}{R}\left[ (1-\lambda)\frac{1}{r_i \sin\theta_j} + \lambda \frac{1}{r_i \cos\theta_j} \right] \right] \right\} \times$$

$$\exp\left[ -(1-\lambda)\frac{t}{r_i \sin\theta_j} - \lambda \frac{t}{r_i \cos\theta_j} \right] \times$$

$$\exp\left[-\frac{(G*TE)^2}{(G_1*TE_1)^2-(G_2*TE_2)^2}\left(\frac{t}{r_i\sin\theta_j}-\frac{t}{r_i\cos\theta_j}\right)\right]$$

From equation (13), we have:

$$\frac{\pi}{4} > \theta > \tan^{-1}\left(\frac{(G_2*TE_2)^2}{(G_1*TE_1)^2}\right). \tag{15}$$

The inversion process becomes unstable near the two boundaries. The problem can be solved by mapping the θ to an infinite space with the following:

$$\theta = \frac{\pi}{4} + \frac{e^{-\theta'}\cdot\left\{\tan^{-1}\left(\frac{(G_2*TE_2)^2}{(G_1*TE_1)^2}\right)-\frac{\pi}{4}\right\}}{1+e^{-\theta'}} \tag{16}$$

where $-\infty < \theta' < \infty$.

Part (c)—Applying Constraints to the Data Processing Method:

In the (r, θ) parameter space, regions can be identified where no fluids can occur. By doing so, the accuracy of the inversion process can be increased.

For example, assuming the intrinsic $T_2$ range for the gas is between 2 seconds and 8 seconds and the diffusivity range for the gas is between $8\times10^{-9}$ m$^2$/s to $10\times10^{-7}$ m$^2$/s, the maximum θ for the gas and the minimum and maximum r for the gas can be estimated. The gas fluid can be bounded by these estimations.

For the water and oil, assuming the maximum diffusivity for water is about $0.5\times10^{-8}$ m$^2$/s, water and oil will be bounded by a (r,θ) curve defined by the maximum diffusivity. The (r,θ) curve is the $$\frac{T_{2,app,TE_1}}{T_{2,app,TE_2}}$$

ratio with the maximum diffusivity.

Therefore, any other regions can be considered as unlikely areas for fluids to occur. Thus, these regions can be excluded from the inversion process.

Figure 7:
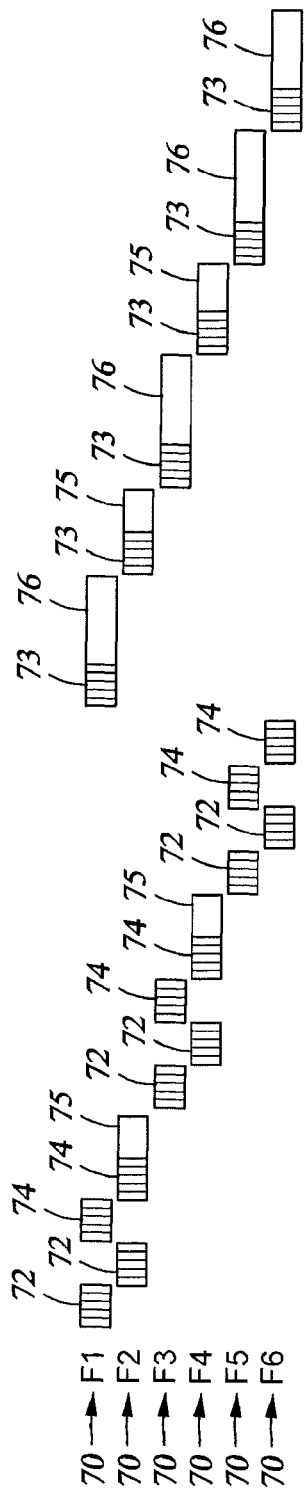
FIG. 7 illustrates a series of six pulse trains used for acquiring NMR data.
Figure 8:
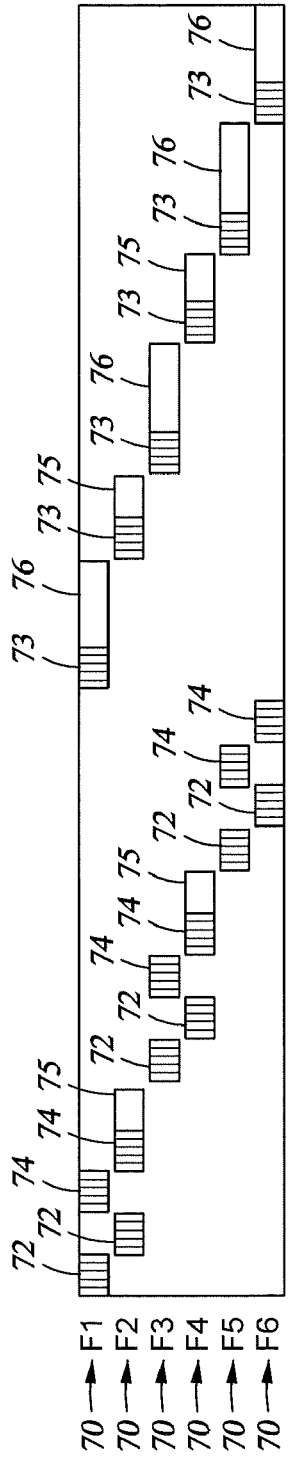
FIG. 8 depicts grouping all the NMR data together for processing.
Figure 9:
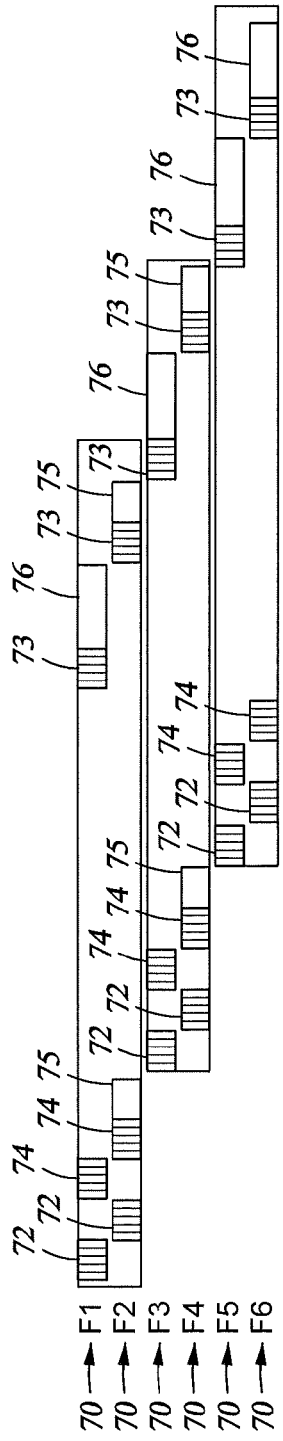
FIG. 9 depicts grouping the NMR data together in groups that use two adjacent frequencies.

FIG. 7 illustrates a series of six pulse sequences 70 used for acquiring NMR data for determining the invasion profile using the techniques disclosed herein. Each pulse sequence 70 includes plurality of trainlets or train of pulses 71. Associated with each train of pulses 71 are an interecho time and a wait time. If differences in invasion are not obvious, then all data can be grouped together for processing as shown in FIG. 8. Three invasion profiles can be obtained from the data acquired from the six pulse trains depicted in FIG. 7 by grouping data by two adjacent frequencies for processing as shown in FIG. 9. An advantage of grouping data is a higher signal-to-noise ratio but at the expense of less resolution of depth of investigation.

For teaching purposes, the embodiments of the techniques were presented using two different interecho times. The two different interecho times can be extended to more than two. Variations of data acquisition parameters can be generated encompassing the techniques presented herein. The essential part of the techniques is to acquire the at least two sets of data using different interecho times that are suitable for fluid identification and quantification.

Figure 10:
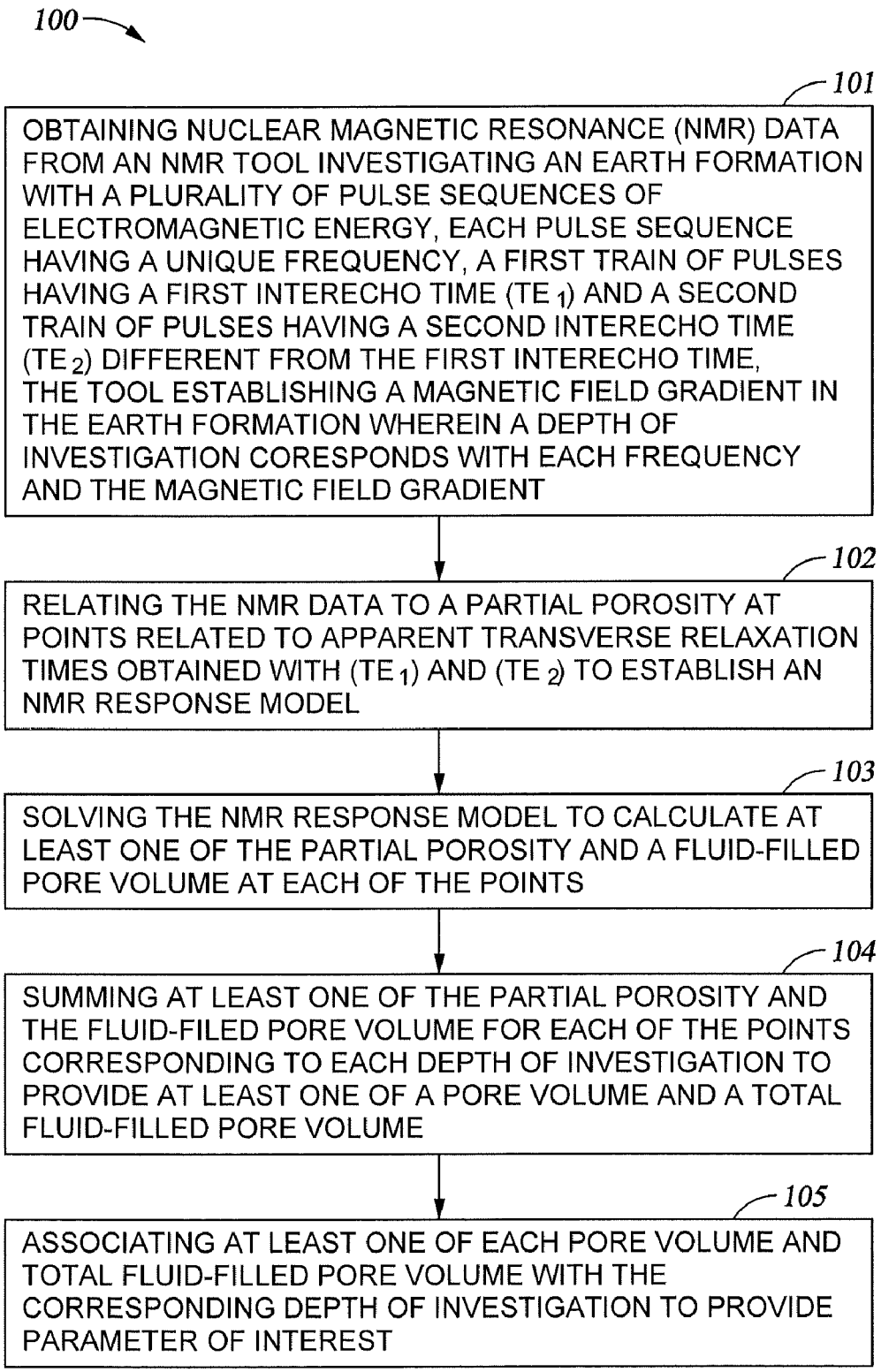
FIG. 10 presents one example of a method for determining a parameter of interest related to a region of interest in an earth formation.

FIG. 10 presents a method 100 for estimating a parameter of interest related to the earth formation 4. The method 100 calls for (step 101) obtaining nuclear magnetic resonance (NMR) data from the NMR tool 10 investigating the earth formation 4 with a plurality of the pulse sequences 70, each pulse sequence 70 having a unique frequency. In each pulse sequence 70, a first train of pulses has a first interecho time ($TE_1$) and a second train of pulses has a second interecho time ($TE_2$) different from the first interecho time. The tool 10 establishes a magnetic field and a magnetic field gradient in the earth formation 4. A depth of investigation corresponds with each frequency and an intensity of the magnetic field. Further, the method 100 calls for (step 102) relating the NMR data to a partial porosity at points (i,j) related to a first apparent transverse relaxation time ($T_{2,app,TE_1,j}$) obtained with ($TE_1$) and a second apparent transverse relaxation time ($T_{2,app,TE_2,i}$) obtained with ($TE_2$) to establish an NMR response model. Further, the method 100 calls for (step 103) solving the NMR response model to calculate at least one of the partial porosity and a fluid-filled pore volume at each of the points. Further, the method 100 calls for (step 104) summing at least one of the partial porosity and the fluid-filled pore volume for each of the points corresponding to each depth of investigation to provide at least one of a pore volume and a total fluid-filled pore volume. Further, the method 100 calls for (step 105) associating at least one of each pore volume and each total fluid-filled pore volume with the corresponding depth of investigation to provide the parameter of interest.

In support of the teachings herein, various analysis components may be used, including a digital and/or analog system. For example, the electronic unit 8 or the processing system 9 may include the digital and/or analog system. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component), magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

Elements of the embodiments have been introduced with either the articles "a" or "an." The articles are intended to mean that there are one or more of the elements. The terms "including" and "having" and their derivatives are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof Therefore, it is intended that the invention not be limited to the particular embodiment disclosed as the best mode contemplated for carrying out this invention, but that the invention will include all embodiments falling within the scope of the appended claims.

What is claimed is:

1. A method for obtaining a parameter of interest related to an earth formation, the method comprising:
    obtaining nuclear magnetic resonance (NMR) data from an NMR tool investigating the earth formation with a plurality of pulse sequences of radio frequency energy, each pulse sequence having a unique frequency, a first train of pulses having a first interecho time ($TE_1$) and a second train of pulses having a second interecho time ($TE_2$) different from the first interecho time, the tool establishing a magnetic field gradient in the earth formation wherein a depth of investigation corresponds with each frequency and the magnetic field gradient;
    relating the NMR data to a partial porosity at points (i,j) related to a first apparent transverse relaxation time ($T_{2,app,TE1,i}$) obtained with ($TE_1$) and a second apparent transverse relaxation time ($T_{2,app,TE2,j}$) obtained with ($TE_2$) to establish an NMR response model;
    solving the NMR response model to calculate at least one of the partial porosity and a fluid-filled pore volume at each of the points;
    summing at least one of the partial porosity and the fluid-filled pore volume for each of the points corresponding to each depth of investigation to provide at least one of a pore volume and a total fluid-filled pore volume; and
    associating at least one of each pore volume and each total fluid-filled pore volume with the corresponding depth of investigation to provide the parameter of interest.

2. The method of claim 1, wherein the fluid is at least one of a gas and a liquid.

3. The method of claim 2, wherein the fluid is a filtrate.

4. The method of claim 1, wherein the partial porosity comprises a function of time t, a wait time (TW) between the trains of pulses, a first magnetic field gradient ($G_1$) applied to the region, a second magnetic field gradient ($G_2$) applied to the region, the first apparent transverse relaxation time ($T_{2,app,TE1,i}$) the second apparent transverse relaxation time ($T_{2,app,TE2,j}$) and a ratio (R) of longitudinal relaxation time to intrinsic transverse relaxation time ($T_1/T_{2int}$) wherein $G_1$ and $T_{2,app,TE1}$, are associated with the train of pulses having the first interecho time ($TE_1$) and $G_2$ and $T_{2,app,TE2,j}$ are associated with the train of pulses having the second interecho time ($TE_2$).

5. The method of claim 4, wherein the NMR relation comprises:

$$M(t, TW, TE, G, R) = \sum_i \sum_j p_{i,j} \left\{ 1 - \exp\left[-\frac{TW}{R}\left[(1-\lambda)\frac{1}{T_{2,app,TE_1,i}} + \lambda \frac{1}{T_{2,app,TE_2,j}}\right]\right] \right\} \times$$

$$\exp\left[-(1-\lambda)\frac{t}{T_{2,app,TE_1,i}} - \lambda \frac{t}{T_{2,app,TE_2,j}}\right] \times \exp$$

$$\left\{-\frac{(G_1 \cdot TE_1)^2 \cdot t}{(G_1 \cdot TE_1)^2 - (G_2 \cdot TE_2)^2}\left(\frac{1}{T_{2,app,TE_1,i}} - \frac{1}{T_{2,app,TE_2,j}}\right)\right\}$$

where $\lambda = \frac{(G_1 \cdot TE_1)^2}{(G_1 \cdot TE_1)^2 - (G_2 \cdot TE_2)^2}$.

6. The method of claim 4, wherein the NMR relation comprises:

$$M(t, TW, TE, G, R) = \sum_i \sum_j p_{i,j} \left\{ 1 - \exp\left[-\frac{TW}{R}\left[(1-\lambda)\frac{1}{r_i \sin\theta_j} + \lambda \frac{1}{r_i \cos\theta_j}\right]\right] \right\} \times$$

$$\exp\left[-(1-\lambda)\frac{t}{r_i \sin\theta_j} - \lambda \frac{t}{r_i \cos\theta_j}\right] \times$$

$$\exp\left[-\frac{(G*TE)^2}{(G_1*TE_1)^2 - (G_2*TE_2)^2}\left(\frac{t}{r_i \sin\theta_j} - \frac{t}{r_i \cos\theta_j}\right)\right]$$

where $\lambda = \frac{(G_1 \cdot TE_1)^2}{(G_1 \cdot TE_1)^2 - (G_2 \cdot TE_2)^2}$, G and TE represent any magnetic field gradient and any interecho time, respectively, used in obtaining the NMR data and r and θ represent polar coordinates.

7. The method of claim 6, wherein G represents $G_1$ and TE represents $TE_1$.

8. The method of claim 1, wherein the first train of pulses is applied prior to the second train of pulses and a duration of the first train of pulses is less than a duration of the second train of pulses.

9. The method of claim 8, wherein the duration of the second train of pulses is at least three times greater than the duration of the first train of pulses.

10. The method of claim 1, wherein solving comprises inversion of the NMR response model.

11. The method of claim 10, further comprising grouping the NMR data into groups having two pulse sequences wherein a difference between frequencies of the two pulse sequences is a minimum with respect to all frequencies used to obtain the NMR data and applying the inversion to each group separately, the grouping being performed prior to the solving.

12. The method of claim 1, further comprising determining a fluid in the pore volume from a ratio of $TE_2/TE_1$.

13. The method of claim 12, wherein the fluid comprises a gas.

14. The method of claim 12, wherein the fluid comprises a liquid.

15. The method of claim 12, further comprising grouping the NMR data into one group prior to the solving, the one group having a higher signal-to-noise ratio than each individual pulse sequence.

16. The method of claim 12, further comprising mapping a distribution of the fluid in an r-θ plane representing the region using polar coordinates.

17. The method of claim 1, wherein the parameter of interest comprises an invasion profile.

18. The method of claim 1, wherein the parameter of interest comprises a boundary of the earth formation.

19. An apparatus for obtaining a parameter of interest related to an earth formation, the apparatus comprising:
a processing system configured to implement the following instructions:
obtaining nuclear magnetic resonance (NMR) data from an NMR tool investigating the earth formation with a plurality of pulse sequences of electromagnetic energy, each pulse sequence having a unique frequency, and a first train of pulses with a first interecho time ($TE_1$) and a second train of pulses having a second interecho time ($TE_2$) different from the first interecho time, the tool establishing a magnetic field gradient in the earth formation wherein a depth of investigation corresponds with each frequency and the magnetic field gradient;
relating the NMR data to a partial porosity at points (i,j) related to a first apparent transverse relaxation time ($T_{2,app,TE1,i}$) obtained with ($TE_1$) and a second apparent transverse relaxation time ($T_{2,app,TE2,j}$) obtained with ($TE_2$) to establish an NMR response model;
solving the NMR response model to calculate at least one of the partial porosity and a fluid-filled pore volume at each of the points in the earth formation;
summing at least one of the partial porosity and the fluid-filled pore volume for each of the points corresponding to each depth of investigation to provide at least one of a pore volume and a total fluid-filled pore volume; and
associating at least one of each pore volume and each total fluid-filled pore volume with the corresponding depth of investigation to provide the parameter of interest.

20. The apparatus of claim 19, further comprising the NMR logging tool.

21. The apparatus of claim 19, wherein the parameter of interest comprises at least one of an invasion profile and a boundary.

22. A non-transitory machine-readable media comprising machine-executable instructions for obtaining a parameter of interest related to an earth formation, by implementing a method comprising:
obtaining nuclear magnetic resonance (NMR) data from an NMR tool investigating the earth formation with a plurality of pulse sequences of electromagnetic energy, each pulse sequence having a unique frequency, and a first train of pulses with a first interecho time ($TE_1$) and a second train of pulses having a second interecho time ($TE_2$) different from the first interecho time, the tool establishing a magnetic field gradient in the earth formation wherein a depth of investigation corresponds with each frequency and the magnetic field gradient;
relating the NMR data to a partial porosity at points (i,j) related to a first apparent transverse relaxation time ($T_{2,app,TE1,i}$) obtained with ($TE_1$) and a second apparent transverse relaxation time ($T_{2,app,TE2,j}$) obtained with ($TE_2$) to establish an NMR response model;
solving the NMR response model to calculate at least one of the partial porosity and a fluid-filled pore volume at each of the points in the earth formation;
summing at least one of the partial porosity and the fluid-filled pore volume for each of the points corresponding to each depth of investigation to provide at least one of a pore volume and a total fluid-filled pore volume; and
associating at least one of each pore volume and each total fluid-filled pore volume with the corresponding depth of investigation to provide the parameter of interest.

\* \* \* \* \*